United States Patent [19]
Bruns et al.

[11] Patent Number: 5,180,663
[45] Date of Patent: Jan. 19, 1993

[54] IMMUNOCHEMICAL ASSAYS FOR HUMAN AMYLASE ISOENZYMES AND RELATED MONOCLONAL ANTIBODIES, HYDRIDOMA CELL LINES AND PRODUCTION THEREOF

[75] Inventors: David Bruns, Charlottesville; David Benjamin, Earlysville, both of Va.

[73] Assignee: University of Virginia Alumni Patents Foundation, Charlottesville, Va.

[21] Appl. No.: 726,160

[22] Filed: Jul. 2, 1991

Related U.S. Application Data

[63] Continuation of Ser. No. 236,303, Aug. 24, 1988, abandoned, which is a continuation of Ser. No. 579,324, Feb. 13, 1984, abandoned.

[51] Int. Cl.$^5$ .......................... C12Q 1/00; C12Q 1/40
[52] U.S. Cl. .................................. 435/7.4; 435/7.5; 435/70.21; 435/172.2; 435/240.1; 435/240.27; 530/388.26
[58] Field of Search .................. 435/240.1, 172.2, 7.4, 435/7.5, 70.21, 240.27; 530/388.26

[56] References Cited
U.S. PATENT DOCUMENTS
4,529,700 8/1982 Gratzner .......................... 935/103

OTHER PUBLICATIONS
Senier et al., Clin. Chem., 27(11):1797–1806 (1981).
Boehm-Truitt et al., Anal. biochem., 85:476–487 (1978).
Karn et al., Biochemical Genetics, 12(6):485–499 (1974).
Carney, Clin. Chim. Acta, 67:153–158 (1976).
Takatsuka et al., Clin. Chim. Acta, 97:261–268 (1979).
Crouse et al., Res. Commun. Chem. Pathol. Pharm., 29(3), 513–525 (1980).
Agarwal et al., Metabolism, 33(3): 797–807 (Sep. 1984).
Zakowsky et al., Clinical Chemistry 30:63, 1984.
Kohler et al., Nature vol. 256, 495–497, 1975.
Chemical Abstracts, vol. 96, 47068a; 1981.
Mednieks et al.–1ADR Abstracts 1984 In J. Dent. Res. vol. 63 (Spec. Issue) 1984 p. 227.
Wako—Chem. Abst. vol. 100 (1984) p. 82015d.

*Primary Examiner*—Sam Rosen
*Attorney, Agent, or Firm*—James Creighton Wray

[57] ABSTRACT

Immunochemical assays for human amylase isoenzymes are disclosed. These assays utilize monoclonal antibodies which are produced from hybridoma cell lines and are specific for human salivary amylase and ovarian tumor amylase but not human pancreatic amylase. The assays involve reacting this monoclonal antibody with the unknown sample for the purpose of studying quantitatively and qualitatively the amylase isoenzymes present. The results from such assays are useful in the diagnosis of disease or ruling out disease. Antibody producing hybridoma cell lines and their production are described.

19 Claims, 1 Drawing Sheet

IMMUNOCHEMICAL ASSAYS FOR HUMAN AMYLASE ISOENZYMES AND RELATED MONOCLONAL ANTIBODIES, HYBRIDOMA CELL LINES AND PRODUCTION THEREOF

This application is a continuation of application Ser. No. 236,303 filed Aug. 24, 1988, which is a continuation of application Ser. No. 579,324 filed Feb. 13, 1984, both now abandoned.

BACKGROUND OF THE INVENTION

Measurements of amylase in serum, urine, other body fluids and tissues have been used for many years as important aids in the diagnosis of a variety of conditions, especially acute pancreatitis. Amylases are usually measured in biological samples by measuring their ability to degrade starch or related compounds. Such assays measure not only amylases produced by the pancreas, but also those amylases produced by, e.g., salivary glands, fallopian tubes, etc. As a result, amylase may be increased in serum or urine when any of these other organs are diseased. This severely limits the diagnostic value of measuring amylase as an aid in the diagnosis of pancreatic disease.

There has been a longstanding need for a simple, rapid, specific method for the measurement of pancreatic amylases in biological samples. However, it has been difficult to distinguish the pancreatic and salivary amylases because of their close similarity. The amylases have been separated by electrophoresis, column chromatography and isoelectric focusing. However, these are, at best, slow and cumbersome. An inhibitor of salivary amylases has been found and applied to the measurement of pancreatic amylase. However, the inhibitor also inhibits pancreatic amylase to a lesser extent. Thus, the inhibitor method does not allow a direct measurement of pancreatic amylases. (We use the term "amylase" to indicate human alpha amylases.)

Therefore, it is an object of this invention to measure pancreatic amylases specifically in the presence of salivary and other amylases without interference from the salivary and other amylases that are closely related to salivary amylases.

It is also a further object of this invention to do this simply, cheaply and rapidly in order that this type of test may be utilized in any routine clinical laboratory set up.

SUMMARY OF THE INVENTION

The present inventors have achieved this invention as a result of their earnest research work to overcome such disadvantages as found with the prior art by developing the monoclonal antibody which reacts with human salivary amylase and ovarian tumor amylase but not human pancreatic amylase.

This invention provides a hybridoma cell line which produces a monoclonal antibody reactive with human salivary but not human pancreatic amylase.

The hybridoma is the fusion product of spleen donor cells from A/J mice, H-$2^a$ haplotype, immunized with the purified human amylase, with SP2/0 myeloma cells H-$2^d$ haplotype.

This invention provides an antibody which reacts with human salivary amylase and ovarian tumor amylase but not with human pancreatic amylase.

The preferred antibody has structural characteristics of the IgG-2a subclass.

An embodiment of the antibody has attached to it an insoluble matrix such as latex or an immunochemical stain.

The immunochemical stain can, for example, be fluorescein or those involved in the avidin-biotin or peroxidase/antiperoxidase immunochemical staining procedures.

Still another embodiment of the antibody has attached to it alkaline phosphatase or a radioisotope where the radioisotope is $^{125}$I or $^{131}$I.

This invention further provides a process for using a monoclonal antibody comprising reacting a monoclonal antibody, which is reactive with human salivary amylase and ovarian tumor amylase but not with human pancreatic amylase, with an unknown sample.

One process provides taking a monoclonal antibody, which is reactive with human salivary amylase and ovarian tumor amylase but not with human pancreatic amylase, which is bound to an insoluble matrix, and reacting it with an unknown sample.

The process could be any competitive protein binding procedure such as radioimmunoassay, enzyme immunoassay or a procedure such as ELISA, i.e., enzyme linked immunosorbent assay.

Other processes to be used are double antibody techniques.

The most useful clinical method is to first determine the total amylase concentration of the unknown sample by any of the routine methods available, then taking the monoclonal antibody which is reactive with human salivary amylase and ovarian tumor amylase but not with human pancreatic amylase and which has also been coupled to an insoluble matrix and reacting this with another portion of the unknown sample, centrifuging the insoluble complex down to a pellet, taking the supernatant and determining the total amylase again by any of the available methods. Total amylase in the supernatant reflects pancreatic amylase in the sample. Subtracting the last concentration determination of pancreatic amylase from the first concentration determination of total amylase results in the determination of the concentration of salivary-type amylase.

The inventors arrived at their invention by first obtaining purified, human salivary amylase (Zakowsky, Gregory and Bruns, *Clinical Chemistry* 30:62, 1984) and immunizing mice with this antigen. The spleens from these mice were excised, and a single cell suspension prepared in serum free medium. These cells were then mixed with SP2/0 myeloma cells at a 2:1 ratio in a centrifuge tube.

The mixture of spleen cells and myeloma cells was centrifuged. The supernatant was then drawn off, and the pellet resuspended in an aliquot of a specific type of polyethylene glycol. The polyethylene glycol promotes fusion of the cells in the mixture. The procedure results in various fusion products, which are: spleen cell-spleen cell hybrids, spleen cell-myeloma cell hybrids and myeloma cell-myeloma cell hybrids.

A selective pressure was set up which effects the isolation of the spleen cell-myeloma cell hybrids, which is the hybridoma. The hybridoma was then cloned by limiting dilution in culture. Antibody from this hybridoma has been produced in several ways: (1) harvesting supernatant from growth of the hybridoma in tissue culture; and (2) induction of an ascites tumor by injection of the hybridoma cells into the peritoneal cavity of a histocompatible CAF$_1$ mouse and harvesting the antibody from the resulting ascitic fluid.

DESCRIPTION OF THE PREFERRED EMBODIMENTS

Figure 1:
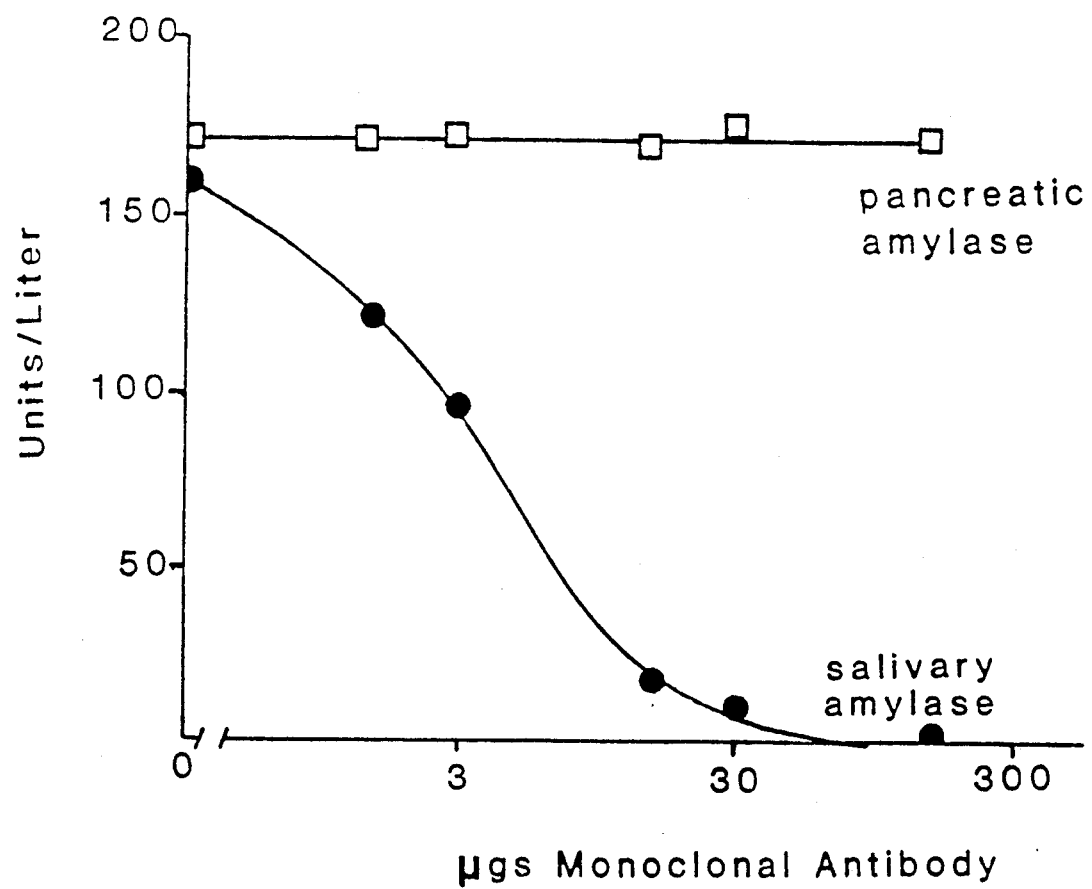
FIG. 1 is a graph depicting the antibody reacting with the salivary amylase but not the pancreatic type amylase.

A monoclonal anti-amylase antibody is used to remove nonpancreatic amylases from samples such as serum, urine and tissue samples. Generally, samples containing amylases are prepared, and their total amylase content is determined by means of any suitable method. Sufficient antibody is then added to bind all of the salivary amylase and ovarian tumor amylase. The amylases that are bound to the antibody are then precipitated by such techniques as those using a second antibody directed against the first antibody. Alternatively, the anti-amylase activity can be coupled or bound to an insoluble support so that the bound amylases are removed from solution without the need of a second antibody, i.e., Staph A, etc.

The pancreatic amylases remaining in the samples are then measured by determining their enzymatic activity (by any convenient method) or by using an antibody-based method or by any other technique that proves capable of measuring amylases generally.

We are also able to use our antibody to measure or detect nonpancreatic amylases without interference from pancreatic amylases using such methods as immunochemical staining and/or standard immunochemical methods including radioimmunoassay (in solution or solid phase) and related immunoassays such as enzyme immunoassays and enzyme linked immunosorbent assays.

The monoclonal antibodies of the present invention were prepared by developing a hybridoma. First, various human amylases were purified, as described in [Zakowski, Gregory and Bruns, *Clinical Chemistry* 30:62, 1984], from saliva, pancreas and serous ovarian cyst fluid. These various human amylases were then used to immunize A/J male mice, H-$2^a$ haplotype. Spleen donor cells were then taken from these mice and fused with SP2/0 myeloma cells, H-$2^d$ haplotype. From this fusion mixture, the hybridoma was selected which produced an anti-salivary antibody which reacts also with ovarian tumor amylase and salivary amylase but not with pancreatic amylase in a standard plate-coating assay. This monoclonal antibody is of the IgG-2a subclass and was further characterized for its ability to distinguish pancreatic amylase from the other, nonpancreatic, amylases. This antibody is referred to below as the HABB antibody. The hybridoma is deposited with American Type Culture Collection, 12301 Parklawn Drive, Rockville, Md. 20852, and has the designation HB-8984.

The HABB antibody was evaluated for its ability to specifically remove human salivary amylase and ovarian tumor amylase from solution while not affecting human pancreatic amylase. This was determined first by adding various amounts of antibody solution to 0.5 ml aliquots of either the pancreatic or the salivary amylase in pure solution. Following a 60-minute incubation at room temperature, 0.05 ml of a Staph A suspension was used to allow precipitation of the antibody-bound amylases. The non-precipitated amylase was then measured in the supernatant by measuring its enzymatic activity.

The HABB antibody, with staph A, completely precipitated salivary amylase but did not precipitate pancreatic amylase. [See FIG. 1.] This same effect was obtained using HABB immobilized on other insoluble matrices, e.g., Sepharose.

To precipitate salivary amylase from serum, HABB was attached to either Staph A or Sepharose. Serum was mixed with either of these materials, and the mixture was centrifuged to remove the antibody and antibody-amylase complexes The amylase isoenzymes in the resulting supernatant were analyzed by electrophoresis which showed that only pancreatic amylase remained.

HABB antibody has been used to study patients with abnormally elevated amounts of amylase in serum in order to determine whether pancreatic amylase was the cause of the increased amylase. For example, one patient with an amylase-secreting tumor was thought to have pancreatitis because of a high serum amylase. Treatment of this patient's serum removed virtually all of the amylase, leading to the correct diagnosis of non-pancreatic hyperamylasemia, which was found to be caused by a gynecological malignancy.

To arrive at the HABB antibody, a purified, human salivary amylase and ovarian tumor amylase had to be obtained. Several routes are available for this appropriation. There are commercially prepared purified amylases, as well as the utilization of one's own laboratory to purify such amylases. Tissue or saliva can be processed and the amylase purified by a combination of standard methods of protein purification combined with affinity chromatography. The purified amylase, then, is used to immunize A/J mice, H-2a haplotype. The mice are then monitored and reimmunized until the desired immune response is obtained. There are a number of ways of monitoring the immune response, but, essentially, this amounts to periodic bleedings and serological testing.

Once the mice are felt to have been sufficiently immunized against the human salivary amylase and ovarian tumor amylase, the spleen is then excised. The spleen contains about $10^8$ lymphocytes. To these spleen cells are added 4 to 5 times $10^7$ SP2/0 myeloma cells, H-$2^d$ haplotype for an approximate 2:1 mixture. This mixture is centrifuged, and the supernatant is drawn off. The cell pellet is then resuspended with slow stirring in $\frac{1}{2}$ ml polyethylene glycol 1000 from Kochlight Industries. The concentration of the polyethylene glycol added is 37% (v/v in serum free medium). The polyethylene glycol promotes fusion of cells resulting in a mixture of various fusion products.

Spleen cell-spleen cell hybrids, myeloma cell-myeloma cell-spleen cell hybrids and myeloma cell-myeloma cell hybrids are obtained. The SP2/0 myeloma cell line used does not produce antibodies of its own and has certain biochemical properties which allow subsequent preferential selection of the desired hybridoma cell line. Because the different fusion products have different characteristics, selective pressure in culture can be effected to isolate the desired hybridoma. The spleen cell-spleen cell combination is not viable in vitro and thus readily dies in tissue culture. When we have eliminated the spleen cell-spleen cell combinations from the mixture, we can utilize the peculiar metabolism of the remaining fusion products to isolate the hybridoma. It is known that the myeloma cell is not able to metabolize certain precursors into essential nutrients. The hybridoma product of the fusion of the myeloma cell with the spleen cell. however, assumes the characteristic of the spleen cell and is capable of synthesizing essential nutrients and the characteristic of the myeloma cell and is capable of essentially immortal growth in culture. By using a selective medium in which to grow the fusion products, the desired hybridoma was isolated. The isolated hybridoma cells were then screened for those that produce antibody to the human salivary amylase and ovarian tumor amylase. Different screening methods can be used. One particularly useful method is the enzyme-linked immunosorbent assay (ELISA assay). This is a standard serological technique using a microtiter plate. Once the desired hybridoma is isolated from the screening procedure, the cell is then cloned by limiting dilution in tissue culture. Hybridoma cells from this final clone were injected into the peritoneal cavity of $CAF_1$ male mice. An ascitis tumor forms in the peritoneal cavity and the antibody is prepared from the resulting ascitic fluid. The antibody purified from the ascitis fluid or from supernatants of tissue culture of the hybridoma cells can be sold as is or as a complex with insoluble matrices or various enzymes, radioisotopes, immunochemical stains, etc. for use in various types of assays e.g., counterimmunoelectrophoresis. The preferred radioisotopes are I125 and I131.

We claim:

1. A hybridoma cell line produced from a hybridoma designated ATCC HB-8984 which produces and secretes HABB monoclonal antibodies reactive with human salivary amylase and ovarian tumor amylase but not human pancreatic amylase.

2. The hybridoma cell line of claim 1 where the hybridoma is the fusion product of spleen donor cells from A/J male mice, $H-2^a$ haplotype, immunized with a purified human amylase, with SP2/0-Ag14 myeloma cells, $H-2^d$ haplotype.

3. A HABB monoclonal antibody which reacts with human salivary amylase and ovarian tumor amylase but not with human pancreatic amylase.

4. The antibody of claim 3 where the structural characteristics of the antibody are of the IgG-2a subclass.

5. The antibody of claim 3 further comprising having attached to it an insoluble matrix whereby said antibody is immobilized yet still reactive.

6. The antibody of claim 5 where the insoluble matrix is an inert material.

7. The antibody of claim 3 further comprising having attached to it an immunochemical stain.

8. The antibody of claim 7 where the immunochemical stain is selected from fluorescein or ones involved in avidin, biotin or peroxidase/antiperoxidase immunochemical staining procedures.

9. The antibody of claim 3 further comprising having attached to it an enzyme for use in assays.

10. The antibody of claim 3 further comprising having attached to it a radioisotope.

11. The antibody of claim 10 wherein the radioisotope comprises 125I or 131I.

12. A process for identifying and measuring specific amylase isoenzymes using HAAB monoclonal antibodies comprising reacting the monoclonal antibodies reactive to human salivary amylase and ovarian tumor amylase but not human pancreatic amylase, with amylases in a biological sample, and measuring the pancreatic amylase.

13. A process of measuring pancreatic amylase comprising first determining the total amylase concentration in a part of a sample and then reacting another part of the same sample with HABB monoclonal antibodies which are reactive to human salivary amylase and ovarian tumor amylase but not human pancreatic amylase, which have also been coupled to an insoluble matrix, centrifuging the insoluble complex down to a pellet, taking the supernatant and determining the total amylase therein which is the pancreatic amylase.

14. A hybridoma having an ATCC designation of HB-8984.

15. HABB monoclonal antibodies produced by hybridoma cell line produced from a hybridoma designated ATCC HB-8984.

16. A hybridoma cell line produced from a hybridoma designated ATCC HB-8984 produced from an ovarian tumor amylase immunogen which produced and secretes monoclonal antibodies reactive with human salivary amylase and ovarian tumor amylase but not reactive with human pancreatic amylase.

17. The hybridoma cell line of claim 16 where the hybridoma is the fusion product of spleen donor cells from A/J male mice, $H-2^a$ haplotype, immunized with a purified human amylase, with SP2/0 Ag14 myeloma cells, $H-2^d$ haplotype.

18. Monoclonal antibodies produced from a hybridoma designated ATCC HB-8984 resulting from an ovarian immunogen which reacts with human salivary amylase and ovarian tumor amylase but not with human pancreatic amylase.

19. A process for identifying and measuring specific amylase isoenzymes using HABB monoclonal antibodies produced from an ovarian immunogen comprising reacting HABB monoclonal antibodies produced from an ovarian immunogen with human salivary amylase and with ovarian tumor amylase but not with human pancreatic amylase in a biological sample, and measuring the amylase remaining in the sample.

* * * * *